US011039779B2

(12) United States Patent
Thakur et al.

(10) Patent No.: US 11,039,779 B2
(45) Date of Patent: Jun. 22, 2021

(54) PULSE PRESSURE VARIABILITY

(71) Applicant: Cardiac Pacemakers, Inc., St. Paul, MN (US)

(72) Inventors: Pramodsingh Hirasingh Thakur, Woodbury, MN (US); Qi An, Blaine, MN (US); David J. Ternes, Roseville, MN (US); Stephen B. Ruble, Lino Lakes, MN (US); Barun Maskara, Princeton Jct, NJ (US)

(73) Assignee: Cardiac Pacemaker, Inc., St. Paul, MN (US)

( * ) Notice: Subject to any disclaimer, the term of this patent is extended or adjusted under 35 U.S.C. 154(b) by 130 days.

(21) Appl. No.: 15/978,851

(22) Filed: May 14, 2018

(65) Prior Publication Data
US 2018/0325402 A1  Nov. 15, 2018

Related U.S. Application Data

(60) Provisional application No. 62/506,333, filed on May 15, 2017.

(51) Int. Cl.
| A61B 5/36 | (2021.01) |
| A61B 5/361 | (2021.01) |
| A61B 5/024 | (2006.01) |
| A61B 5/021 | (2006.01) |
| A61B 5/0245 | (2006.01) |
(Continued)

(52) U.S. Cl.
CPC ............ *A61B 5/361* (2021.01); *A61B 5/0245* (2013.01); *A61B 5/02108* (2013.01); *A61B 5/02133* (2013.01); *A61B 5/02427* (2013.01); *A61B 5/352* (2021.01); *A61B 5/681* (2013.01); *A61B 5/686* (2013.01); *A61B 5/6826* (2013.01); *A61B 5/0031* (2013.01); *A61B 5/021* (2013.01); *A61B 5/02416* (2013.01); *A61B 5/02438* (2013.01);
(Continued)

(58) Field of Classification Search
None
See application file for complete search history.

(56) References Cited

U.S. PATENT DOCUMENTS 7,826,899 B1   11/2010  Ryu et al.
8,060,197 B2   11/2011  Ben-David et al.
(Continued)

FOREIGN PATENT DOCUMENTS

| CN | 110621224 A | 12/2019 |
| WO | WO-2016100720 A1 | 6/2016 |
| WO | WO-2018213169 A1 | 11/2018 |

OTHER PUBLICATIONS

"International Application Serial No. PCT/US2018/032527, International Preliminary Report on Patentability dated Nov. 28, 2019", 9 pgs.

(Continued)

*Primary Examiner* — Ankit D Tejani
(74) *Attorney, Agent, or Firm* — Schwegman Lundberg & Woessner, P.A.

(57) ABSTRACT

This document discusses, among other things, systems and methods to receive physiologic information of a patient, to receive pulse pressure information from the patient different than the received physiologic information, and to determine an indication of atrial fibrillation (AF) using the received physiologic information and the received pulse pressure information.

14 Claims, 3 Drawing Sheets

(51) Int. Cl.
*A61B 5/00* (2006.01)
*A61B 5/352* (2021.01)
*A61B 7/04* (2006.01)
*A61B 5/283* (2021.01)

(52) U.S. Cl.
CPC ............. *A61B 5/283* (2021.01); *A61B 5/6824* (2013.01); *A61B 7/04* (2013.01)

(56) References Cited

U.S. PATENT DOCUMENTS

| | | |
|---|---|---|
| 2006/0253300 A1 | 11/2006 | Somberg et al. |
| 2008/0147140 A1 | 6/2008 | Ternes et al. |
| 2010/0063840 A1 | 3/2010 | Hoyme et al. |
| 2013/0041269 A1 | 2/2013 | Stahmann et al. |
| 2013/0204328 A1 | 8/2013 | Stahmann et al. |
| 2015/0065891 A1 | 3/2015 | Wiesel |
| 2015/0297096 A1 | 10/2015 | Chakravarthy et al. |
| 2015/0342466 A1* | 12/2015 | Thakur ............... A61B 5/024 600/484 |
| 2016/0045125 A1 | 2/2016 | Krueger et al. |
| 2016/0058391 A1 | 3/2016 | Narusawa et al. |

OTHER PUBLICATIONS

"International Application Serial No. PCT/US2018/032527, International Search Report dated Sep. 12, 2019", 4 pgs.

"International Application Serial No. PCT/US2018/032527, Written Opinion dated Sep. 12, 2019", 8 pgs.

Dodge, Harold, et al., "Ventricular Dynamics in Atrial Fibrillation", Circulation, vol. X V,, (Mar. 1957), 335-347.

Falicov, M.D., et al., "Relationship of the Pulmonary Artery End-Diastolic Pressure to the Left Ventricular End-Diastolic and Mean Filling Pressures in Patients With and Without Left Ventricular Dysfunction", Circulation, XLII, (Jul. 1970), 65-73.

Waggoner, A. D, et al., "Improvements in left ventricular diastolic function after cardiac resynchronization therapy are coupled to response in systolic performance", J Am Coll Cardiol., 46(12), (Dec. 20, 2005), 2244-9.

"European Application Serial No. 18731558.5, Response to Communication Pursuant to Rules 161 and 162 filed Jul. 7, 2020", 14 pgs.

* cited by examiner

PULSE PRESSURE VARIABILITY

CLAIM OF PRIORITY

This application claims the benefit of priority under 35 U.S.C. § 119(e) of U.S. Provisional Patent Application Ser. No. 62/506,333, filed on May 15, 2017, which is herein incorporated by reference in its entirety.

TECHNICAL FIELD

This document relates generally to medical devices, and more particularly, but not by way of limitation, to systems, devices, and methods of pulse pressure variability assessment.

BACKGROUND

Atrial fibrillation (AF) can be described as an abnormal heart rhythm characterized by rapid and irregular activity in the upper chambers, the left and right atria, of the heart, affecting more than 25 million people in Europe and North American alone. AF is commonly associated with a reduction in cardiac output, an increased risk of heart failure (HF), dementia, and stroke. Risk factors for AF include, among others, high blood pressure, heart failure (HF), valvular heart disease, COPD, obesity, and sleep apnea.

SUMMARY

This document discusses, among other things, systems and methods to receive physiologic information of a patient, to receive pulse pressure information from the patient different than the received physiologic information, and to determine an indication of atrial fibrillation (AF) using the received physiologic information and the received pulse pressure information.

An example (e.g., "Example 1") of subject matter (e.g., a system) may include a first ambulatory medical device (AMD) configured to detect physiologic information from a patient, and a second AMD, different than the first AMD, configured to detect pulse pressure information from the patient, wherein the first AMD is configured to receive pulse pressure information from the second AMD, and to determine an AF indication using the detected physiologic information and the detected pulse pressure information. The second AMD can optionally include at least one of: an optical sensor; a pressure sensor; an acoustic sensor; an impedance sensor; a vibratory sensor; or a strain sensor.

In Example 2, the subject matter of Example 1 may optionally be configured such that the first AMD includes an implantable cardiac monitor (ICM) configured to detect physiologic information from the patient, and the second AMD includes a wearable medical device configured to detect pulse pressure information from the patient.

In Example 3, the subject matter any one or more of Examples 1-2 may optionally be configured such that the wearable medical device includes at least one of a wrist-worn medical device or a finger-worn medical device configured to detect a photoplethysmogram (PPG) signal from the patient.

In Example 4, the subject matter any one or more of Examples 1-3 may optionally be configured such that the ICM is configured to determine the AF indication using the detected physiologic information, and to augment the determined AF indication using the received pulse pressure information.

In Example 5, the subject matter any one or more of Examples 1-4 may optionally be configured such that the ICM is configured to confirm or deny the determined AF indication using the received pulse pressure information from the wearable medical device.

In Example 6, the subject matter any one or more of Examples 1-5 may optionally be configured such that the first AMD includes an AF circuit configured to determine an AF indication using the detected physiologic information, and to augment the AF determination using the received pulse pressure information.

In Example 7, the subject matter any one or more of Examples 1-6 may optionally be configured such that the ICM is configured to detect at least one of electrocardiogram (ECG) information or heart sound (HS) information from the patient, and to determine the AF indication using the detected ECG information, the detected HS information, or the detected ECG and HS information.

An example (e.g., "Example 8") of subject matter (e.g., a medical device) may include an atrial fibrillation (AF) circuit configured to receive physiologic information from a patient, and a signal receiver circuit configured to receive pulse pressure information from the patient, the received pulse pressure information different than the received physiologic information, wherein the AF circuit is configured to determine an AF indication using the received physiologic information and the received pulse pressure information.

In Example 9, the subject matter of Example 8 may optionally be configured such that the AF circuit is configured to determine the AF indication using the received physiologic information, and to augment the determined AF indication using the received pulse pressure information.

In Example 10, the subject matter any one or more of Examples 8-9 may optionally be configured such that the AF circuit is configured to confirm or deny the determined AF indication using the received pulse pressure information.

In Example 11, the subject matter any one or more of Examples 8-10 may optionally be configured such that the AF circuit is configured to augment the AF determination using the received pulse pressure information.

In Example 12, the subject matter any one or more of Examples 8-11 may optionally be configured such that the AF circuit is configured to determine the AF indication using the received physiologic information and a threshold, wherein the AF circuit is configured to adjust the threshold using the received pulse pressure information.

An example (e.g., "Example 13") of subject matter (e.g., a method) may include: receiving physiologic information from a patient using an atrial fibrillation (AF) circuit; receiving pulse pressure information from the patient using a signal receiver circuit, the received pulse pressure information different than the received physiologic information; and determining, using the AF circuit, an AF indication using the received physiologic information and the received pulse pressure information.

In Example 14, the subject matter of Example 13 may optionally be configured to include: detecting physiologic information from the patient using a first ambulatory medical device (AMD); and detecting pulse pressure information from the patient using a second AMD, different than the first AMD.

In Example 15, the subject matter any one or more of Examples 13-14 may optionally be configured such that the first AMD includes an implantable cardiac monitor (ICM), and the second AMD includes a wearable medical device.

In Example 16, the subject matter any one or more of Examples 13-15 may optionally be configured such that the wearable medical device includes at least one of a wrist-worn medical device or a finger-worn medical device, and the detecting pulse pressure information includes detecting a photoplethysmogram (PPG) signal from the patient using the wearable medical device.

In Example 17, the subject matter any one or more of Examples 13-16 may optionally be configured such that detecting physiologic information includes detecting at least one of electrocardiogram (ECG) information or heart sound (HS) information from the patient using the ICM, and determining the AF indication using the received physiologic information includes using the detected ECG information, the detected HS information, or the detected ECG and HS information.

In Example 18, the subject matter any one or more of Examples 13-17 may optionally be configured such that the determining the AF indication using the received physiologic information and the received pulse pressure information includes: determining the AF indication using the received physiologic information; and augmenting the initial AF indication using the received pulse pressure information.

In Example 19, the subject matter any one or more of Examples 13-18 may optionally be configured such that the augmenting the AF indication includes confirming or denying the determined AF indication using the received pulse pressure information.

In Example 20, the subject matter any one or more of Examples 13-19 may optionally be configured such that the determining the AF indication using the received physiologic information and the received pulse pressure information includes: determining the AF indication using the received physiologic information; and augmenting the determining the AF indication using the received pulse pressure information.

An example (e.g., "Example 21") of subject matter (e.g., a system or apparatus) may optionally combine any portion or combination of any portion of any one or more of Examples 1-20 to include "means for" performing any portion of any one or more of the functions or methods of Examples 1-20, or a "non-transitory machine-readable medium" including instructions that, when performed by a machine, cause the machine to perform any portion of any one or more of the functions or methods of Examples 1-20.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
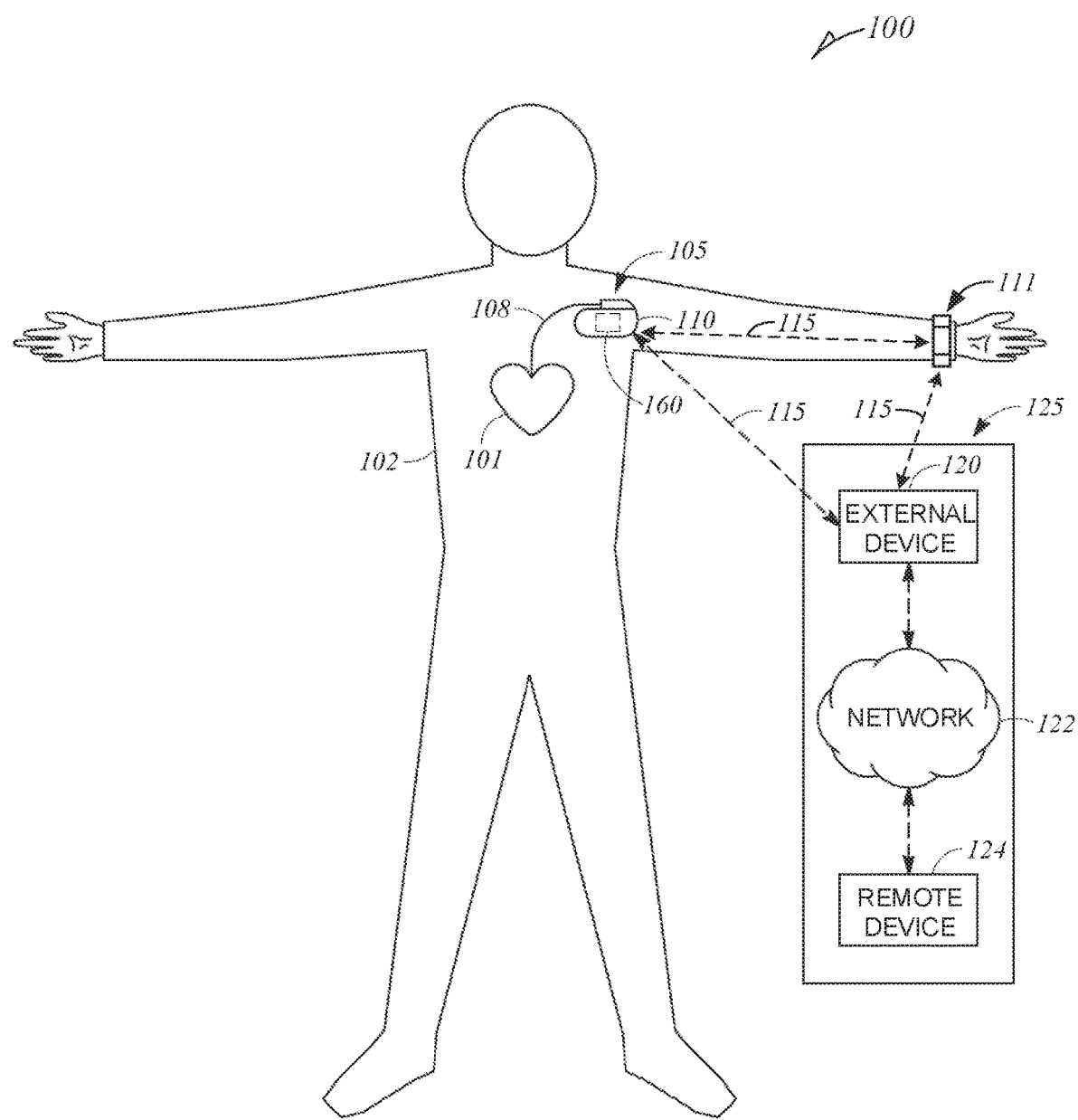
FIG. 1 illustrates an example patient management system.

The present inventors have recognized, among other things, detecting atrial fibrillation (AF) using pulse pressure information from a patient. In an example, an ambulatory medical device (AMD) can sense a pulsatile signal, such as a photoplethysmogram (PPG) or other pulsatile signal indicative of changes in blood volume in a patient, and the AMD, or one or more other AMD or external device, can detect AF, or alter or augment AF detection, using information from the sensed pulsatile signal.

In an example, the AMD can include a wearable, wrist- or finger-worn medical device configured to detect a PPG signal of a patient. The AMD, or a device coupled to the AMD (e.g., one or more other AMD, such as an implantable cardiac monitor (ICM), another AMD, or external or wearable medical device, or an external medical-device programmer or one or more other external device configured to communicate with an ICM or other AMD using Bluetooth or one or more other communication protocol, etc.), can determine a pulse pressure signal using information from the AMD, such as information about the detected PPG signal. Pulse pressure information, such as pulse pressure variability (PPV) information, can be used to detect AF in a patient, to alter or augment AF detection in an ICM or one or more other AMD or external device, or to alter or augment information detected by the ICM or one or more other AMD or external device used to determine AF.

For example, when an ICM detects AF, information from the AMD (e.g., a wrist- or finger-worn or other external medical device) can be used to confirm/deny the original AF detection using pulse pressure information (e.g., PPG signal variability). If the ICM determines an indication of AF, and pulse pressure information from the AMD is also indicative of AF, the ICM determination can be confirmed. If the ICM determines an indication of AF, and pulse pressure information from the AMD is not indicative of AF, the ICM determination can be denied. Over time, the prevalence of confirmation or denial of AF detection by the ICM (or AF detection using ICM information) can be used to refine AF detection in either a specific patient, or across a target population. In an example, a higher incidence of denials can be used to increase an AF detection threshold in the ICM or using ICM information, for example, to improve detection specificity. In contrast, a higher incidence of confirmations can be used to reduce an AF detection threshold in the ICM or using ICM information, for example, to increase detection sensitivity.

In other examples, the AMD (e.g., a wrist-worn medical device) can be configured to receive patient assessment information (e.g., AF symptom assessment), such as in response to a query by the AMD, and the received assessment information (e.g., "I can tell an event is happening, but am okay"; "I am bad"; "The event is getting worse"; etc.) can be used to augment AF detection, such as by augmenting an algorithm used to detect AF in the ICM or one or more other AMD or external device, or by augmenting information detected by the ICM or one or more other AMD or external devices used to determine or classify AF. In an example, AF can be classified using one or more AF characteristics, such as rate, stability, duration, pulse pressure information, etc. The received patient assessment information can be correlated to or otherwise associated with patient physiologic information to improve or augment patient-specific or population-based AF detection, therapy, or intervention.

The present inventors have recognized, among other things, that an R-wave can be detected, or R-wave detection (e.g., in an ICM or other AMD, or using ICM or AMD information) can be improved using pulse pressure information. For example, ICM or AMD R-wave detections can be checked against beat detection using pulse pressure information (e.g., a PPG signal) to confirm R-wave detection accuracy or to adjust one or more detection thresholds in the ICM or AMD.

In certain examples, pulse pressure information can include information about, or a change in, one or more of: a pulse pressure or peak pulse pressure amplitude or variability; an area of a pulse pressure or pulse pressure variability signal (e.g., relative to a multiple beat average, a rolling floor, etc.); a timing between a pulse pressure or pulse pressure variability fiducial and one or more other fiducials (e.g., an electrical, mechanical, or second pulse pressure fiducial, etc.); or a slope or other signal characteristic of the pulse pressure or peak pulse pressure amplitude or variability, or correlation of the pulse pressure signal characteristic and one or more other physiologic signal characteristic or fiducial; etc.

FIG. 1 illustrates an example patient management system 100 and portions of an environment in which the system 100 may operate. The patient management system 100 can perform a range of activities, including remote patient monitoring and diagnosis of a disease condition. Such activities can be performed proximal to a patient 102, such as in a patient home or office, through a centralized server, such as in a hospital, clinic, or physician office, or through a remote workstation, such as a secure wireless mobile computing device.

The patient management system 100 can include an ambulatory system 105, an external system 125, and a communication link 115 providing for communication between the ambulatory system 105 and the external system 125.

The ambulatory system 105 can include an implantable medical device (IMD) 110, a wearable medical device 111, or one or more other implantable, leadless, subcutaneous, external, or wearable medical device configured to monitor, sense, or detect information from, or provide one or more therapies to treat various cardiac conditions relating to an ability of a heart 101 to sufficiently deliver blood to a body, such as atrial fibrillation (AF), congestive heart failure (CHF), or one or more other cardiac conditions.

In an example, the IMD 110 can include one or more traditional cardiac rhythm management (CRM) devices, such as a pacemaker, defibrillator, or cardiac monitor, implanted in a chest of a patient, having a lead system 108 including one or more transvenous, subcutaneous, or non-invasive leads or catheters to position one or more electrodes or other sensors in, on, or about a heart 101 or one or more other position in a thorax, abdomen, or neck of a patient 102.

The IMD 110 can include a detector circuit 160 configured to detect an event or process physiologic information received from the patient 102. In an example, the medical event includes a specific cardiac arrhythmia. Examples of cardiac arrhythmias can include atrial or ventricular brady- or tachy-arrhythmia, such as atrial fibrillation (AF), atrial flutter, atrial tachycardia, supraventricular tachycardia, ventricular tachycardia, or ventricular fibrillation, among others. In an example, the cardiac arrhythmia detection circuit 160 is configured to detect worsening of a chronic medical condition, such as heart failure (HF). In another example, the medical event can include patient-triggered events.

The IMD 110 can alternatively be configured as a therapeutic device configured to treat arrhythmia or other heart conditions. The IMD 110 may additionally include a therapy unit that may generate and deliver one or more therapies. The therapy can be delivered to the patient 102 via the lead system 108 and associated electrodes, or using one or more other delivery mechanisms. The therapy can include anti-arrhythmic therapy to treat an arrhythmia or to treat or control one or more complications from arrhythmias, such as syncope, congestive heart failure (CHF), or stroke, among others. Examples of the anti-arrhythmic therapy include pacing, cardioversion, defibrillation, neuromodulation, drug therapies, or biological therapies, among other types of therapies. In other examples, therapies can include cardiac resynchronization therapy (CRT) for rectifying dyssynchrony and improving cardiac function in CHF patients. In some examples, the IMD 110 can include a drug delivery system, such as a drug infusion pump to deliver drugs to the patient for managing arrhythmias or complications from arrhythmias.

In other examples, the ambulatory system 105 can include one or more leadless cardiac pacemakers (LCP) or other small (e.g., smaller than traditional implantable CRM devices), self-contained device configured to detect physiologic information from or provide one or more therapies or stimulation to the heart 101 without traditional lead or implantable CRM device complications (e.g., required incision and pocket, complications associated with lead placement, breakage, or migration, etc.). An LCP may have more limited power and processing capabilities than a traditional CRM device; however, multiple LCP devices can be implanted in or about the heart 101 to detect physiologic information from, or to provide one or more therapies or stimulations to, one or more chambers of the heart 101. The multiple LCP devices can communicate between themselves, or one or more other implanted or external devices.

The wearable medical device 111 can include one or more wearable or external medical sensors or devices (e.g., automatic external defibrillators (AEDs), Holter monitors, patch-based devices, smart watches, smart accessories, wrist- or finger-worn medical devices, etc.) configured to detect or monitor physiologic information of the patient without required implant or an in-patient procedure for placement, battery replacement, or repair. In an example, the wearable medical device 111 can include an optical sensor configured to detect a photoplethysmogram (PPG) signal on a wrist, finger, or other location on the patient, the PPG signal including pressure variations from which pulse pressure information can be detected. In other examples, the wearable medical device 111 can include any device configured to detect pulsatile variations of pressure of the patient, including an acoustic sensor or accelerometer to detect the sound or vibration of blood flow, an impedance sensor to detect impedance variations associated with changes in blood flow or volume, a temperature sensor to detect temperature variation associated with blood flow, a laser Doppler vibrometer or other pressure, strain, or physical sensor to detect physical variations associated with blood flow, etc. The wearable medical device 111 can be located on or about an artery, a vein, or one or more other anatomical location where blood flow information can be detected. In other examples, the pulse pressure information can be detected using one or more implantable or other ambulatory medical devices.

The patient management system 100 can include, among other things, a respiration sensor configured to receive respiration information (e.g., a respiration rate (RR), a respiration volume (tidal volume), etc.), a heart sound sensor configured to receive heart sound information, a thoracic impedance sensor configured to receive impedance information, a cardiac sensor configured to receive cardiac electrical information, and an activity sensor configured to receive information about a physical motion (e.g., activity, posture, etc.), or one or more other sensors configured to receive physiologic information of the patient 102.

The external system 125 can include a dedicated hardware/software system, such as a programmer, a remote server-based patient management system, or alternatively a system defined predominantly by software running on a standard personal computer. The external system 125 can manage the patient 102 through the IMD 110 connected to the external system 125 via a communication link 115. In other examples, the IMD 110 can be connected to the wearable device 111, or the wearable device 111 can be connected to the external system 125, via the communication link 115. This can include, for example, programming the IMD 110 to perform one or more of acquiring physiological data, performing at least one self-diagnostic test (such as for a device operational status), analyzing the physiological data to detect a cardiac arrhythmia, or optionally delivering or adjusting a therapy to the patient 102. Additionally, the external system 125 can send information to, or receive information from, the IMD 110 or the wearable device 111 via the communication link 115. Examples of the information can include real-time or stored physiological data from the patient 102, diagnostic data, such as detection of cardiac arrhythmias or events of worsening heart failure, responses to therapies delivered to the patient 102, or device operational status of the IMD 110 or the wearable device 111 (e.g., battery status, lead impedance, etc.). The communication link 115 can be an inductive telemetry link, a capacitive telemetry link, or a radio-frequency (RF) telemetry link, or wireless telemetry based on, for example, "strong" Bluetooth or IEEE 802.11 wireless fidelity "Wi-Fi" interfacing standards. Other configurations and combinations of patient data source interfacing are possible.

By way of example and not limitation, the external system 125 can include an external device 120 in proximity of the IMD 110, and a remote device 124 in a location relatively distant from the IMD 110 in communication with the external device 120 via a telecommunication network 122. Examples of the external device 120 can include a medical device programmer.

The remote device 124 can be configured to evaluate collected patient information and provide alert notifications, among other possible functions. In an example, the remote device 124 can include a centralized server acting as a central hub for collected patient data storage and analysis. The server can be configured as a uni-, multi-, or distributed computing and processing system. The remote device 124 can receive patient data from multiple patients including, for example, the patient 102. The patient data can be collected by the IMD 110, among other data acquisition sensors or devices associated with the patient 102. The server can include a memory device to store the patient data in a patient database. The server can include an alert analyzer circuit to evaluate the collected patient data to determine if specific alert condition is satisfied. Satisfaction of the alert condition may trigger a generation of alert notifications. In some examples, the alert conditions may alternatively or additionally be evaluated by the IMD 110. By way of example, alert notifications can include a Web page update, phone or pager call, E-mail, SMS, text or "Instant" message, as well as a message to the patient and a simultaneous direct notification to emergency services and to the clinician. Other alert notifications are possible. The server can include an alert prioritizer circuit configured to prioritize the alert notifications. For example, an alert of a detected medical event can be prioritized using a similarity metric between the physiological data associated with the detected medical event to physiological data associated with the historical alerts.

The remote device 124 may additionally include one or more locally configured clients or remote clients securely connected over the network 122 to the server. Examples of the clients can include personal desktops, notebook computers, mobile devices, or other computing devices. System users, such as clinicians or other qualified medical specialists, may use the clients to securely access stored patient data assembled in the database in the server, and to select and prioritize patients and alerts for health care provisioning. Example systems are described in commonly-assigned U.S. application Ser. No. 11/121,593, "System and Method for Managing Coordination of Assembled Patient Data in an Automated Patient Management System," filed May 3, 2005, and U.S. application Ser. No. 11/121,594, "System and Method for Managing Patient Triage in an Automated Patient Management System," filed May 3, 2005, the disclosures of which are hereby incorporated by reference in their entirety. In addition to generating alert notifications, the remote device 124, including the server and the interconnected clients, may also execute a follow-up scheme by sending follow-up requests to the IMD 110, or by sending a message or other communication to the patient 102, clinician or authorized third party as a compliance notification.

The network 122 can provide wired or wireless interconnectivity. In an example, the network 122 can be based on the Transmission Control Protocol/Internet Protocol (TCP/IP) network communication specification, although other types or combinations of networking implementations are possible. Similarly, other network topologies and arrangements are possible.

One or more of the external device 120 or the remote device 124 can output the detected medical events to a system user, such as the patient or a clinician, or to a process including, for example, an instance of a computer program executable in a microprocessor. In an example, the process can include an automated generation of recommendations for anti-arrhythmic therapy, or a recommendation for further diagnostic test or treatment. In an example, the external device 120 or the remote device 124 can include a respective display unit for displaying the physiological or functional signals, or alerts, alarms, emergency calls, or other forms of warnings to signal the detection of arrhythmias. In some examples, the external system 125 can include an external data processor configured to analyze the physiological or functional signals received by the IMD 110, and to confirm or reject the detection of arrhythmias. Computationally intensive algorithms, such as machine-learning algorithms, can be implemented in the external data processor to process the data retrospectively to detect cardia arrhythmias.

Portions of the IMD 110 or the external system 125 can be implemented using hardware, software, firmware, or combinations thereof. Portions of the IMD 110 or the external system 125 can be implemented using an application-specific circuit that can be constructed or configured to perform one or more functions, or can be implemented using a general-purpose circuit that can be programmed or otherwise configured to perform one or more functions. Such a general-purpose circuit can include a microprocessor or a portion thereof, a microcontroller or a portion thereof, or a programmable logic circuit, a memory circuit, a network interface, and various components for interconnecting these components. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals.

In an example, the patient management system 100 can include a wrist- or finger-worn medical device as an alternative to an implantable loop recorder or a Holter or patch device. The patient 102 can be instructed to prompt, wear, or put on a wrist- or finger-worn medical device when not feeling well rather than carry or wear a Holter or other patch device at all times. The wrist- or finger-worn medical device can communicate with an external system 125 or an external device 120, such as a mobile device, to send or receive patient input or information, to receive information about or confirm patient status or patient symptoms, etc.

Arterial pulse pressure has a significant linear relationship to a preceding diastolic interval. A longer diastolic interval can be indicative of increased ventricle filling. Increased ventricle filling can provide a stronger contraction (e.g., Starling mechanism). A stronger contraction can provide for greater stroke output. A greater stroke output can provide a larger arterial pulse pressure swing. Accordingly, a high heart rate (HR) in AF can be associated with lower arterial pulse pressure swings (e.g., a reduced pulse pressure variability).

High heart rates during certain atrial fibrillation (AF) therapies, such as atrial-tachycardia response (ATR) mode, can adversely impact filling times. As HR increases, a period between a heart sound (HS) (e.g., a first heart sounds (S1), a second heart sound (S2), a third heart sound (S3), a fourth heart sounds (S4), etc.) and the next R-wave can become disproportionally smaller with respect to HR. In an example, the period between the second heart sound (S2) of a first cardiac cycle and the R-wave of the proceeding cardiac cycle (S2-R) can disproportionately decrease with respect to heart rate as the heart rate increases, negatively impacting filling. Thus, the present inventors have recognized, among other things, a need to closely monitor the impact of programming changes in response to AF. Further, one or more heart sounds (HS) (e.g., S1, S2, S3, S4, etc.) measurements or characteristics can be used to detect AF, including HS amplitude, variability, timing (e.g., S4 timing, etc.), changes in HS amplitude or variability, or a timing between two or more separate HS fiducials or a HS fiducial and one or more other electrical or other signal characteristic (e.g., diastolic intervals, etc.).

Pulse pressure information can be used to detect AF, to augment AF detection, or to confirm/deny AF detection. Arterial pulsations during exercise are likely to be similar or increased due to preserved diastolic filling and increased cardiac output. Arterial filling times are higher during sinoatrial (SA) driven higher heart rate (e.g., higher adrenergic state) than in an AF driven higher heart rate. Accordingly, changes in pulse pressure information with respect to HR changes can be used to detect AF, or to augment or confirm/deny AF.

In an example, N beats can be sorted based on HR. Peak-to-peak pressure changes in a certain number or percentage of the top n/N beats (e.g., having high HR) can be compared to peak-to-peak pressure changes in a certain number or percentage of the bottom n/N beats (e.g., having a low HR). In an example, if the peak-to-peak pressure changes in the top n/N beats is lower than the peak-to-peak pressure changes in the bottom n/N beats, AF can be detected or confirmed; otherwise, exercise can be detected or confirmed.

In other examples, beat-to-beat variability in arterial pulse pressure swings can be measured, and AF can be detected or confirmed if the beat-to-beat variability exceeds a threshold. In certain examples, pulse pressure variability itself can be used to detect AF. In an example, pulse pressure variability can be used as a secondary screen after detecting a sharp HR or R-R variability change as a primary detection. Use of primary and secondary screening measures, or multiple sensor inputs in a single detection algorithm, can reduce the burden of measuring a high resolution primary signal, such as if the primary measurement is energy or resource intensive.

In an example, HR (e.g., an increase in HR) or variability (e.g., a decrease in R-R variability) can be indicative of AF, such as described in the commonly-assigned U.S. application Ser. No. 14/825,669, "Atrial Fibrillation Detection Using Ventricular Rate Variability," filed Aug. 13, 2015, the disclosure of which his hereby incorporated by reference in its entirety. In an example, pulse pressure information can be used, in conjunction with one or more other physiologic measure, such as HR, R-R variability, HS, etc., to determine AF.

In an example, a carotid or cervical impedance measurement, such as detected using a cuff electrode, can be used as a surrogate for arterial pressure. An autonomic modulation therapy (AMT) system can be configured to detect or confirm AF using changes in arterial pressure to titrate HF therapy in the presence of AF. Neural therapy, or one or more other cardiac or drug therapies, can be modulated to target AF. For example, pulse pressure variability can be used to control mode switching between a first therapy mode, such as a chronic HF therapy mode, and an acute AF abolition mode. Patients having a high chronic prevalence of AF can be detected, and AMT therapy can be adjusted using the arterial pressure information.

In an example, implantable or external electrodes can be used to detect impedance variations of, on, or about a vessel or an artery (e.g., the descending arch of the aorta). The impedance variations can be indicative of changes in blood volume in a patient, including stroke volume (SV), cardiac output (CO), or pulse pressure information using the detected impedance variations.

In other examples, detected pressure pulsations can reflect irregularity of right ventricle (RV) output during AF. Accordingly, in patients having a sole pulmonary artery (PA) pressure sensor, AF can be detected using the detected pressure pulsations. Pulse pressure variations can be used to guide differential treatment strategies in HF patients with or without AF. For example, therapy can be adjusted to minimize pulse pressure variation within the range of therapy control.

Figure 2:
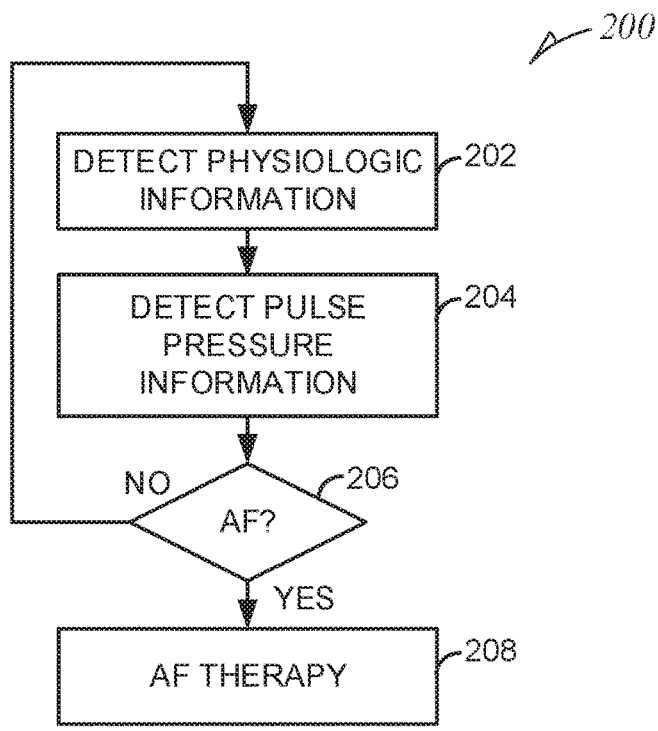
FIGS. 2-3 illustrate example methods of detecting atrial fibrillation (AF) in a patient.

FIG. 2 illustrates an example method 200 of detecting atrial fibrillation (AF) in a patient. At 202, physiologic information can be detected. At 204, pulse pressure information can be detected. In an example, the physiologic information can be different from the pulse pressure information. The physiologic information can be detected using a first ambulatory medical device (AMD), and the pulse pressure information can be detected using a second AMD, different than or separate from the first AMD. In an example, the first AMD can include an implantable cardiac monitor (ICM) configured to be implanted in the patient. In other examples, the first AMD can include one or more other implanted or external medical devices configured for long-term patient monitoring. In an example, the second AMD can include a wearable medical device separate from the first AMD. The second AMD can include a wrist-worn or finger-worn medical device configured to sense or detect pulse pressure information from the patient, such as a photoplethysmogram (PPG) signal from a wrist or a finger of the patient.

At 206, an indication of AF can be determined using the detected physiologic information and the detected pulse pressure information. In an example, the indication of AF can be determined using a comparison of one or more signal characteristics (e.g., a short-term average, etc.) or features to a threshold. In an example, the threshold can include a patient-specific baseline (e.g., a long-term average, etc.), a population baseline, a patient-specific or population-based template, or one or more other thresholds. In an example, the indication of AF can be determined using a combination of the detected physiologic information and the detected pulse pressure information to a threshold. In other examples, the indication of AF can be determined using the detected physiologic information and a threshold, and the determined indication can be augmented (e.g., confirmed or denied) using the pulse pressure information. In an example, augmenting can include adjusting the physiologic information used to determine the indication of AF, adjusting the threshold, or otherwise adjusting or altering the determined AF indication using the detected pulse pressure information.

If, at 206, no AF is determined, then process flow can return to 202. If, at 206, AF is determined at 206, the, at 208, AF therapy can be provided to the patient, such as using one or more leads or electrodes of an implantable medical device, etc. In other examples, an alert or notification of AF can be provided to a user, a machine or automated process, or a clinician or other caregiver, etc.

Figure 3:
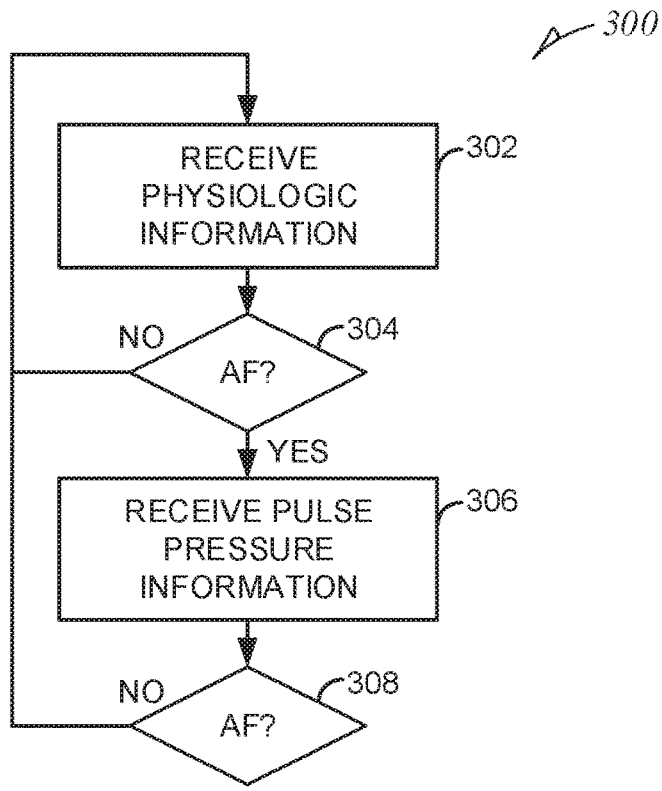

FIG. 3 illustrates an example method 300 of detecting atrial fibrillation (AF) in a patient. At 302, physiologic information can be received from a patient, for example, at one or more ambulatory, external, or remote medical device or system.

At 304, an indication of atrial fibrillation (AF) can be determined, for example, using an AF circuit in one or more ambulatory, external, or remote medical device or system, such as by comparing one or more characteristic, measure, or feature of the received physiologic information to a threshold. If, at 304, no AF is determined, then process flow can return to 302. If, at 304, AF is determined, then, at 306, pulse pressure information can be received from the patient.

In an example, collection of pulse pressure information from the patient can be prompted by a machine or automated process, such as notifying the user to begin detection of pulse pressure information using a wrist- or finger-worn medical device following detection of AF using the received physiologic information. In other examples, the patient can be instructed to begin detection of pulse pressure information upon feeling abnormal. In such situation, where a user prompts AF detection, the pulse pressure information can trigger a higher resolution AF determination using received physiologic information. A user can prompt AF determination using one or more inputs, beginning detection of pulse pressure information, or by simply waking up or turning on a wearable device configured to detect pulse pressure information.

At 308, an initial determination of AF, such as using the received physiologic information, can be augmented using the received pulse pressure information. In an example, the received pulse pressure information can be used to confirm or deny an initial determination of AF, or otherwise alter AF detection. If, at 308, no AF is determined, then process flow can return to 302. If, at 308, AF is determined, one or more AF therapies or patient alerts or interventions can be provided.

Figure 4:
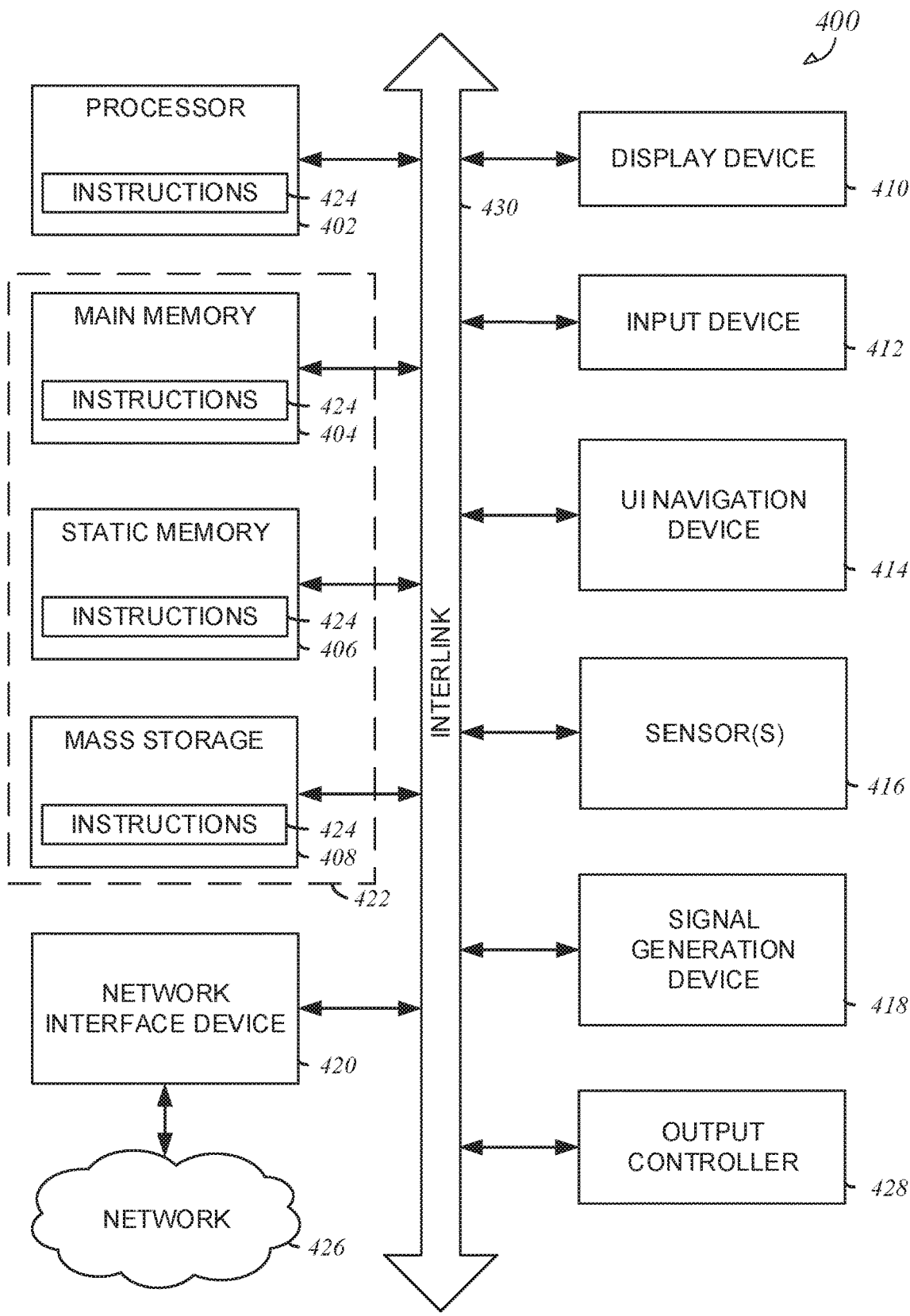
FIG. 4 illustrates a block diagram of an example machine upon which any one or more of the techniques discussed herein may perform.

FIG. 4 illustrates a block diagram of an example machine 400 upon which any one or more of the techniques (e.g., methodologies) discussed herein may perform. Portions of this description may apply to the computing framework of one or more of the medical devices described herein, such as the IMD, the external programmer, etc.

Examples, as described herein, can include, or may operate by, logic or a number of components, or mechanisms in the machine 400. Circuitry (e.g., processing circuitry) is a collection of circuits implemented in tangible entities of the machine 400 that include hardware (e.g., simple circuits, gates, logic, etc.). Circuitry membership can be flexible over time. Circuitries include members that may, alone or in combination, perform specified operations when operating. In an example, hardware of the circuitry can be immutably designed to carry out a specific operation (e.g., hardwired). In an example, the hardware of the circuitry can include variably connected physical components (e.g., execution units, transistors, simple circuits, etc.) including a machine-readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuitry in hardware via the variable connections to carry out portions of the specific operation when in operation. Accordingly, in an example, the machine-readable medium elements are part of the circuitry or are communicatively coupled to the other components of the circuitry when the device is operating. In an example, any of the physical components can be used in more than one member of more than one circuitry. For example, under operation, execution units can be used in a first circuit of a first circuitry at one point in time and reused by a second circuit in the first circuitry, or by a third circuit in a second circuitry at a different time. Additional examples of these components with respect to the machine 400 follow.

In alternative embodiments, the machine 400 may operate as a standalone device or can be connected (e.g., networked) to other machines. In a networked deployment, the machine 400 may operate in the capacity of a server machine, a client machine, or both in server-client network environments. In an example, the machine 400 may act as a peer machine in peer-to-peer (P2P) (or other distributed) network environment. The machine 400 can be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

The machine (e.g., computer system) 400 can include a hardware processor 402 (e.g., a central processing unit (CPU), a graphics processing unit (GPU), a hardware processor core, or any combination thereof), a main memory 404, a static memory (e.g., memory or storage for firmware, microcode, a basic-input-output (BIOS), unified extensible firmware interface (UEFI), etc.) 406, and mass storage 408 (e.g., hard drive, tape drive, flash storage, or other block devices) some or all of which may communicate with each other via an interlink (e.g., bus) 430. The machine 400 may further include a display unit 410, an alphanumeric input device 412 (e.g., a keyboard), and a user interface (UI) navigation device 414 (e.g., a mouse). In an example, the display unit 410, input device 412, and UI navigation device 414 can be a touch screen display. The machine 400 may additionally include a signal generation device 418 (e.g., a speaker), a network interface device 420, and one or more sensors 416, such as a global positioning system (GPS) sensor, compass, accelerometer, or other sensor. The machine 400 can include an output controller 428, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

Registers of the processor 402, the main memory 404, the static memory 406, or the mass storage 408 may be, or include, a machine-readable medium 422 on which is stored one or more sets of data structures or instructions 424 (e.g., software) embodying or utilized by any one or more of the techniques or functions described herein. The instructions 424 may also reside, completely or at least partially, within any of registers of the processor 402, the main memory 404, the static memory 406, or the mass storage 408 during execution thereof by the machine 400. In an example, one or any combination of the hardware processor 402, the main memory 404, the static memory 406, or the mass storage 408 may constitute the machine-readable medium 422. While the machine-readable medium 422 is illustrated as a single medium, the term "machine-readable medium" can include a single medium or multiple media (e.g., a centralized or distributed database, and/or associated caches and servers) configured to store the one or more instructions 424.

The term "machine-readable medium" can include any medium that is capable of storing, encoding, or carrying instructions for execution by the machine 400 and that cause the machine 400 to perform any one or more of the techniques of the present disclosure, or that is capable of storing, encoding or carrying data structures used by or associated with such instructions. Non-limiting machine-readable medium examples can include solid-state memories, optical media, magnetic media, and signals (e.g., radio frequency signals, other photon based signals, sound signals, etc.). In an example, a non-transitory machine-readable medium comprises a machine-readable medium with a plurality of particles having invariant (e.g., rest) mass, and thus are compositions of matter. Accordingly, non-transitory machine-readable media are machine-readable media that do not include transitory propagating signals. Specific examples of non-transitory machine-readable media can include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 424 can be further transmitted or received over a communications network 426 using a transmission medium via the network interface device 420 utilizing any one of a number of transfer protocols (e.g., frame relay, internet protocol (IP), transmission control protocol (TCP), user datagram protocol (UDP), hypertext transfer protocol (HTTP), etc.). Example communication networks can include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 420 can include one or more physical jacks (e.g., Ethernet, coaxial, or phone jacks) or one or more antennas to connect to the communications network 426. In an example, the network interface device 420 can include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 400, and includes digital or analog communications signals or other intangible medium to facilitate communication of such software. A transmission medium is a machine-readable medium.

Various embodiments are illustrated in the figures above. One or more features from one or more of these embodiments can be combined to form other embodiments. Method examples described herein can be machine or computer-implemented at least in part. Some examples can include a computer-readable medium or machine-readable medium encoded with instructions operable to configure an electronic device or system to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:
1. A system, comprising:
a first ambulatory medical device (AMD) comprising an implantable cardiac monitor (ICM) configured to detect physiologic information from a patient and to determine an initial atrial fibrillation (AF) indication using the detected physiologic information;
a second AMD comprising a wearable medical device, different than the first AMD, configured to detect pulse pressure information from the patient; and
an AF circuit configured to confirm the determined initial AF indication using pulse pressure information from the second AMD,
wherein the AF circuit is configured to:
receive physiologic information from N beats of the patient, the physiologic information comprising heart rate (HR) information of the N beats;

receive pulse pressure information of the N beats of the patient; and sort the N beats based on HR into at least two groups comprising:
  a high HR group comprising one or more of the N beats having a relative high HR with respect to the N beats; and
  a low HR group comprising one or more of the N beats having a relative low HR with respect to the N beats; and determine a difference between pulse pressure information from the high HR group and pulse pressure information from the low HR group, and wherein the AF circuit is configured to confirm the determined initial AF indication using the determined difference between pulse pressure information from the high HR group and pulse pressure information from the low HR group.

2. The system of claim 1, wherein the wearable medical device includes at least one of a wrist-worn medical device or a finger-worn medical device configured to detect a photoplethysmogram (PPG) signal from the patient.

3. The system of claim 1, wherein the first AMD is configured to detect at least one of electrocardiogram (ECG) information or heart sound (HS) information from the patient, and to determine the initial AF indication using the detected ECG information, the detected HS information, or the detected ECG and HS information.

4. The system of claim 1, wherein the first AMD is configured to determine the initial AF indication using the received physiologic information and a threshold, and
  wherein the AF circuit is configured to adjust the threshold using the received pulse pressure information.

5. The system of claim 1, wherein the first AMD comprises the AF circuit.

6. A system, comprising:
  an atrial fibrillation (AF) circuit configured to receive physiologic information of a patient from a first ambulatory medical device (AMD); and
  a signal receiver circuit configured to receive pulse pressure information of the patient from a second AMD, different than the first AMD, the received pulse pressure information different than the received physiologic information,
  wherein the AF circuit is configured to determine a change in the received pulse pressure information and to determine an AF indication using the determined change in the received pulse pressure information with respect to the received physiologic information,
  wherein the AF circuit is configured to receive physiologic information from N beats of the patient, the physiologic information comprising heart rate (HR) information of the N beats,
  wherein the signal receiver circuit is configured to receive pulse pressure information of the N beats of the patient,
  wherein the AF circuit is configured to sort the N beats based on HR into at least two groups comprising:
    a high HR group comprising one or more of the N beats having a relative high HR with respect to the N beats; and
    a low HR group comprising one or more of the N beats having a relative low HR with respect to the N beats,
  wherein, to determine the change in the received pulse pressure information, the AF circuit is configured to determine a difference between pulse pressure information from the high HR group and pulse pressure information from the low HR group, and
  wherein the AF circuit is configured to determine the AF indication using the determined difference.

7. The medical device of claim 6, wherein the AF circuit is configured to determine the AF indication using the received physiologic information, and to confirm the determined AF indication using the received pulse pressure information.

8. The medical device of claim 6, wherein the AF circuit is configured to determine the AF indication using the received physiologic information and a threshold, and
  wherein the AF circuit is configured to adjust the threshold using the received pulse pressure information.

9. The system of claim 6, comprising the first AMD and the second AMD,
  wherein the first AMD comprises an implantable cardiac monitor (ICM) configured to detect physiologic information from the patient, and
  wherein the second AMD comprises a wearable medical device configured to detect pulse pressure information from the patient.

10. The system of claim 9, wherein the first AMD comprises the AF circuit.

11. A method, comprising:
  receiving, using an atrial fibrillation (AF) circuit, physiologic information of a patient from a first ambulatory medical device (AMD);
  receiving, using a signal receiver circuit, pulse pressure information of the patient from a second AMD, different than the first AMD, the received pulse pressure information different than the received physiologic information; and
  determining, using the AF circuit, an initial AF indication using the received physiologic information; and
  confirming, using the AF circuit, the determined initial AF indication using the received pulse pressure information,
  wherein receiving physiologic information of the patient comprises receiving physiologic information from N beats of the patient, the physiologic information comprising heart rate (HR) information of the N beats,
  wherein receiving pulse pressure information of the patient comprises receiving pulse pressure information of the N beats of the patient,
  wherein confirming the determined initial AF indication using the received pulse pressure information comprises:
    sorting the N beats based on HR into at least two groups comprising:
      a high HR group comprising one or more of the N beats having a relative high HR with respect to the N beats; and
      a low HR group comprising one or more of the N beats having a relative low HR with respect to the N beats; and
    determining a difference between pulse pressure information from the high HR group and pulse pressure information from the low HR group,
    wherein confirming the determined initial AF indication comprises using the determined difference between pulse pressure information from the high HR group and pulse pressure information from the low HR group.

12. The method of claim 11, wherein the first AMD includes an implantable cardiac monitor (ICM), and the second AMD includes a wearable medical device,
  wherein the wearable medical device includes at least one of a wrist-worn medical device or a finger-worn medical device configured to detect a photoplethysmogram (PPG) signal from the patient.

13. The method of claim 11, wherein receiving physiologic information includes receiving at least one of electrocardiogram (ECG) information or heart sound (HS) information from the patient using the first AMD, and wherein determining the initial AF indication using the received physiologic information includes using the detected ECG information, the detected HS information, or the detected ECG and HS information.

14. The method of claim 11, wherein determining the initial AF indication comprises using the received physiologic information and a threshold, the method further comprising:

adjusting, using the AF circuit, the threshold using the received pulse pressure information.

* * * * *